(12) United States Patent
Hoffman et al.

(10) Patent No.: US 6,522,715 B2
(45) Date of Patent: Feb. 18, 2003

(54) HIGH DENSITY FLEX INTERCONNECT FOR CT DETECTORS

(75) Inventors: David M. Hoffman, New Berlin, WI (US); Bing Shen, Cary, NC (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 0 days.

(21) Appl. No.: 10/125,951

(22) Filed: Apr. 19, 2002

(65) Prior Publication Data

US 2002/0163993 A1 Nov. 7, 2002

Related U.S. Application Data

(63) Continuation-in-part of application No. 09/751,824, filed on Dec. 29, 2000.

(51) Int. Cl.$^7$ .................... G01N 23/00; A61B 6/03
(52) U.S. Cl. .................... 378/19; 378/4; 250/370.11; 439/492
(58) Field of Search .................. 378/4, 19; 250/370.09, 250/370.11; 439/492, 493

(56) References Cited

U.S. PATENT DOCUMENTS

| 5,668,851 | A | * | 9/1997 | Dobbs et al. | ................... | 378/19 |
| 6,061,419 | A | * | 5/2000 | Hsieh et al. | .................... | 378/4 |
| 6,144,718 | A | * | 11/2000 | Hoffman et al. | .............. | 378/19 |
| 6,173,031 | B1 | * | 1/2001 | Hoffman et al. | .............. | 378/19 |

* cited by examiner

*Primary Examiner*—Drew A. Dunn
(74) *Attorney, Agent, or Firm*—Carl B. Horton, Esq.; Armstrong Teasdale LLP

(57) ABSTRACT

A detector module includes a photosensor array having a first width, and a flexible cable operationally coupled to the photosensor array, wherein the cable has a width greater then the first width.

20 Claims, 6 Drawing Sheets

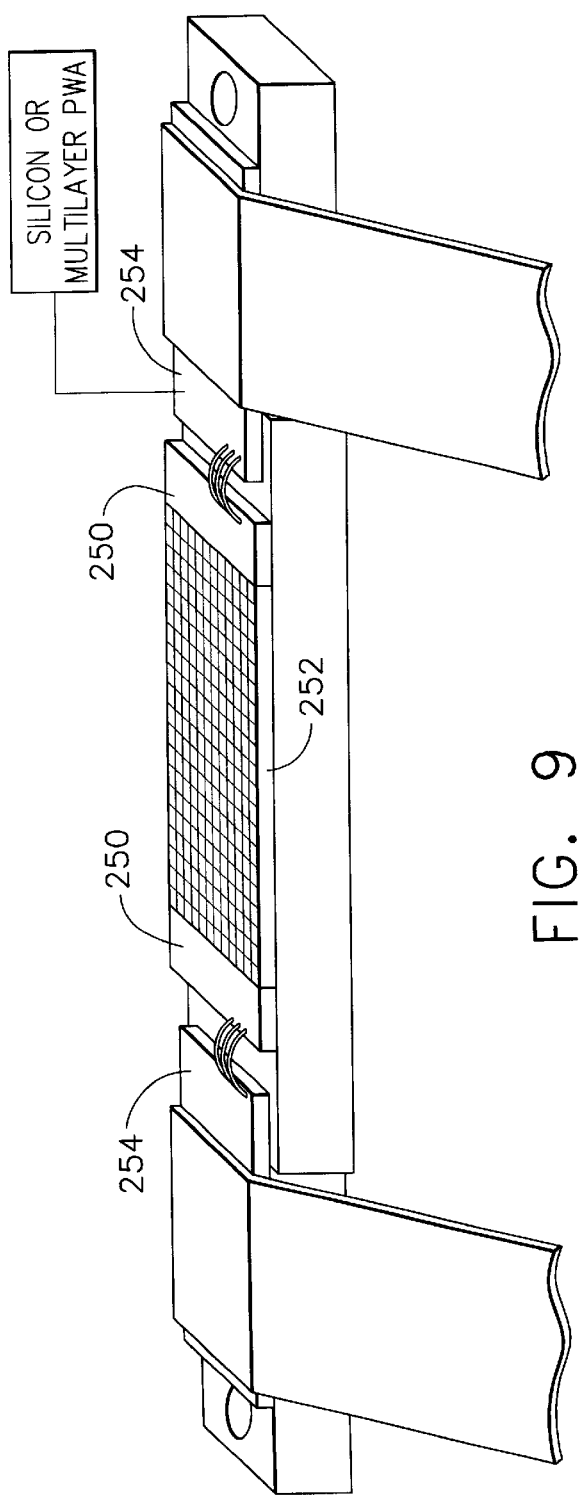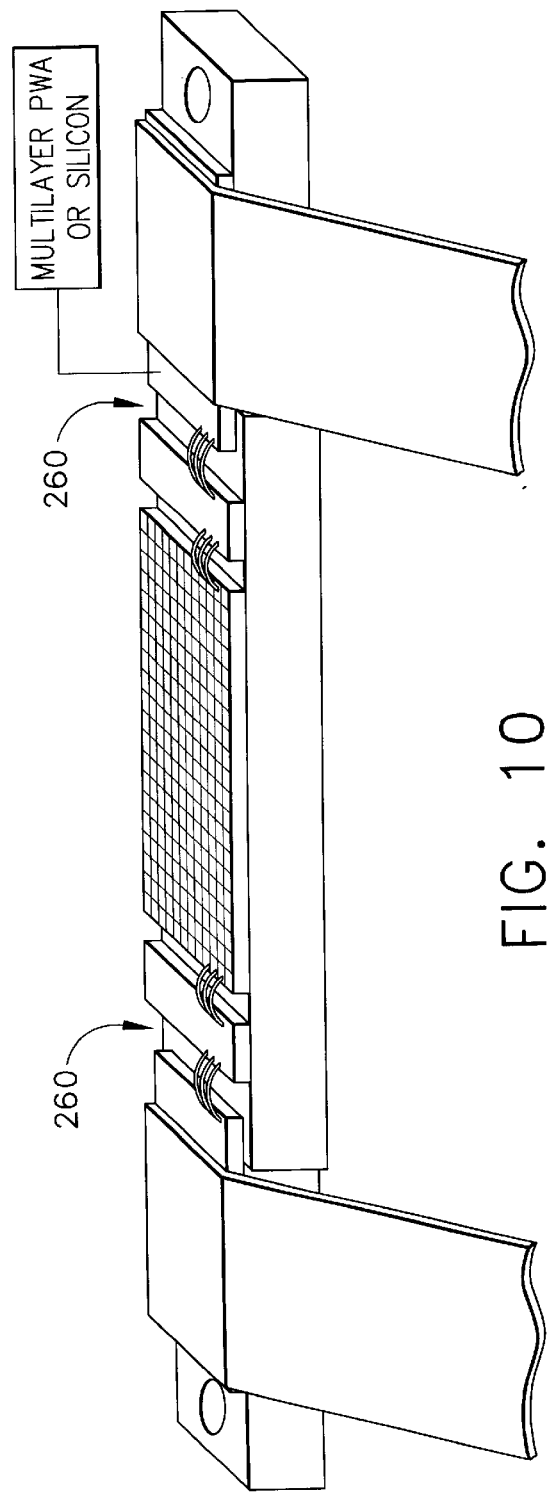

HIGH DENSITY FLEX INTERCONNECT FOR CT DETECTORS

CROSS REFERENCE TO RELATED APPLICATIONS

This application is a Continuation In Part of U.S. patent application Ser. No. 09/751,824 filed Dec. 29, 2000.

BACKGROUND OF THE INVENTION

This invention relates generally to scintillating type radiation detectors, and, more particularly, to a high density flex interconnect system for computer tomograph CT detectors and to methods for preparing and using the herein described high density flex interconnect system.

At least one known detector in CT imaging systems includes a plurality of detector modules, each having a scintillator array optically coupled to a semiconductor photodiode array that detects light output by the scintillator array. These photodiode arrays are electrically connected to a CT system data acquisition system (DAS) through flex circuits. The photodiode arrays in one known module is wire bonded to a Field Effect Transistor (FET) array silicon chip, that is in turn wire bonded to a flex circuit. The diode array along with FET chips on both ends and flex circuits on both ends are all mounted on a ceramic substrate. The wire bond interconnect density and the flex run density are very near the current state of the art. It is therefore desirable to at least partially eliminate these density limits.

BRIEF SUMMARY OF THE INVENTION

In one aspect, a detector module includes a photosensor array having a first width, and a flexible cable operationally coupled to the photosensor array, wherein the cable has a width greater then the first width.

In another aspect, a photosensor module configured for use in a computed tomography system having a DAS system for receiving data is provided. The module includes a substrate having a photodiode array thereon optically coupled to a scintillator array, a FET chip electrically connected to the photodiode array and mounted on the substrate, and a high density interconnect, and a flex circuit connected to the DAS system. The flex interconnect is mounted on the substrate wherein the longitudinal axis of the flex circuit is perpendicular to the horizontal axis of the substrate and diode.

In a further aspect, A Computed Tomographic (CT) system includes a radiation source, and a detector array positioned to receive radiation from said source. The detector array includes a plurality of detector modules each including a photosensor array having a first width, and a flexible cable operationally coupled to the photosensor array. The cable having a width greater then the first width.

BRIEF DESCRIPTION OF THE DRAWINGS

FIG. 9 is a perspective view of a module similar to the module depicted in FIG. 6.

FIG. 10 is a perspective view of a module similar to the module depicted in FIG. 6.

DETAILED DESCRIPTION OF THE INVENTION

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two-dimensional slice taken through the object. One method of reconstructing an image from a set of projection data is referred to in the art as the filtered back projection technique. This process converts the attenuation measurements from a scan into integers called "CT numbers" or "Hounsfield" units that are used to control the brightness of a corresponding pixel in a cathode ray tube display.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Figure 1:
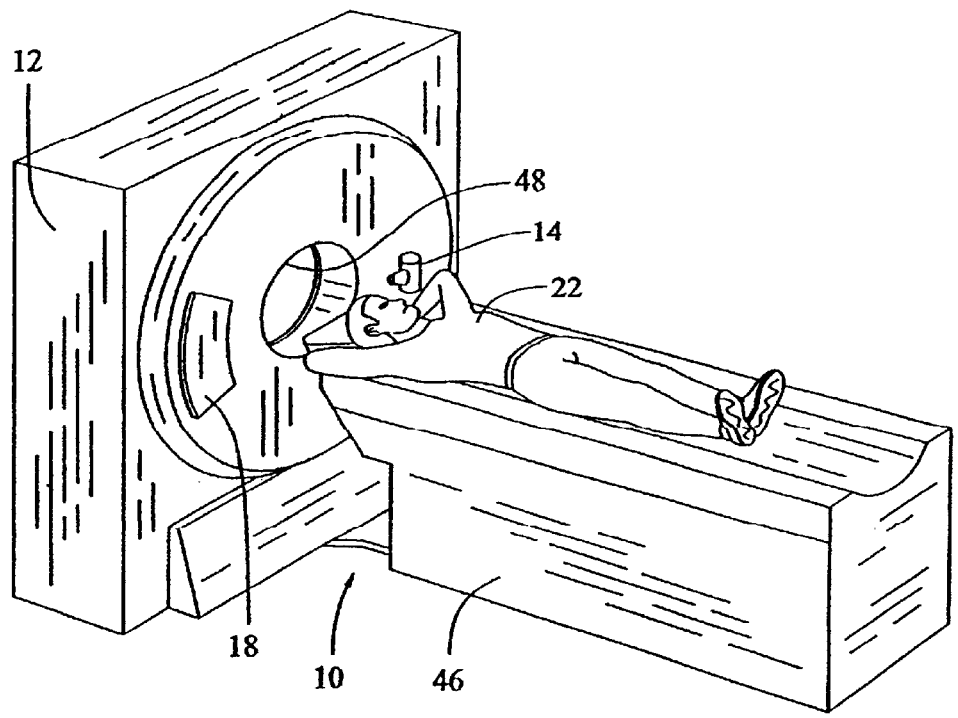
FIG. 1 is a pictorial view of a CT imaging system.
Figure 2:
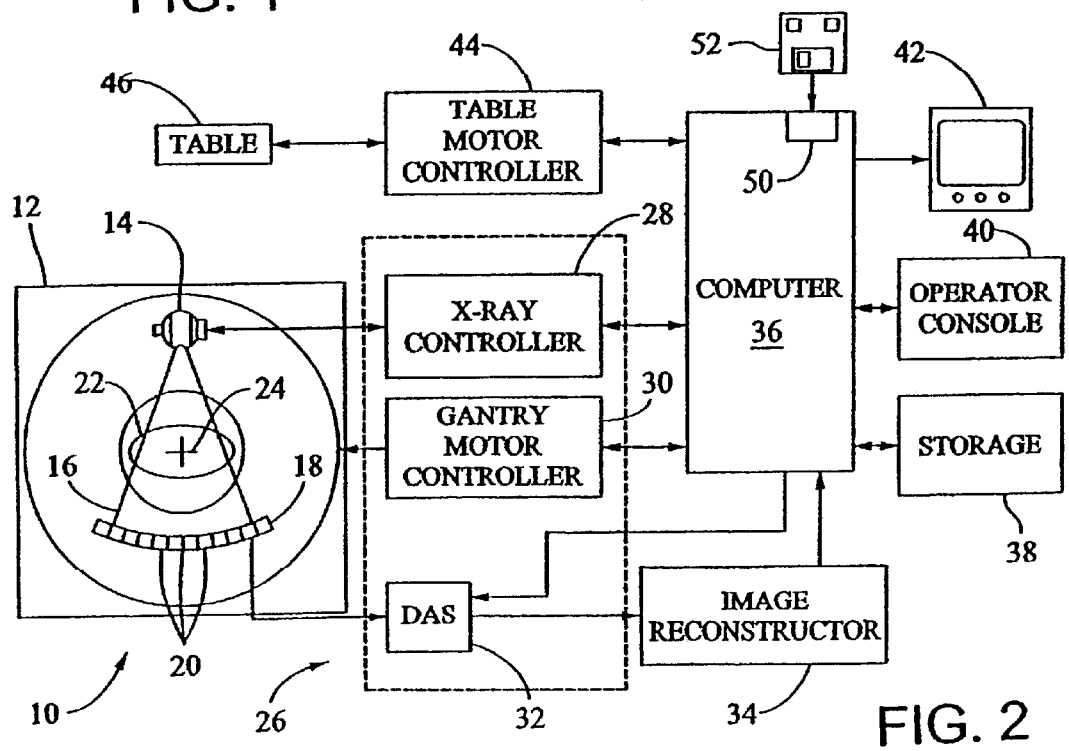
FIG. 2 is a block schematic of the system illustrated in FIG. 1.

Referring to FIGS. 1 and 2, a multi-slice scanning imaging system, for example, computed tomography (CT) imaging system 10, is shown as including a gantry 12 representative of a "third generation" CT imaging system. Gantry 12 has an x-ray source 14 that projects a beam of x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. FIG. 2 shows only a single row of detector elements 20 (i.e., a detector row). However, multislice detector array 18 includes a plurality of parallel detector rows of detector elements 20 so that projection data corresponding to a plurality of quasi-parallel or parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data received from detector elements 20 through a flex cable (not shown in FIGS. 1 and 2), and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits.

Figure 3:
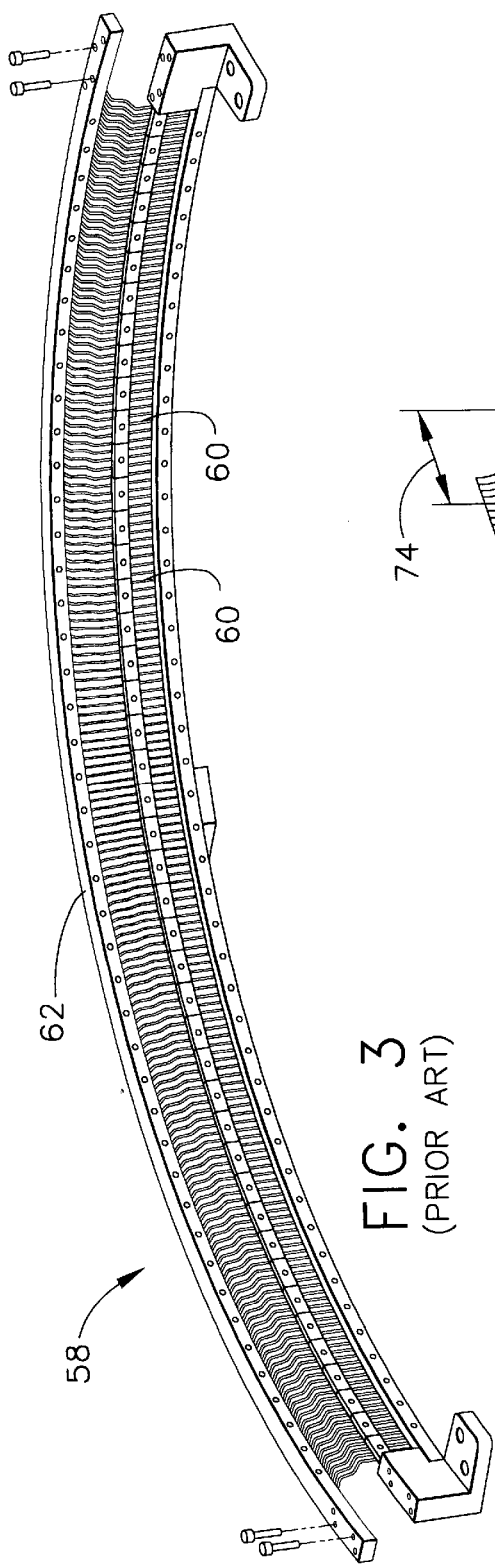
FIG. 3 is a perspective view of a prior art detector array.
Figure 4:
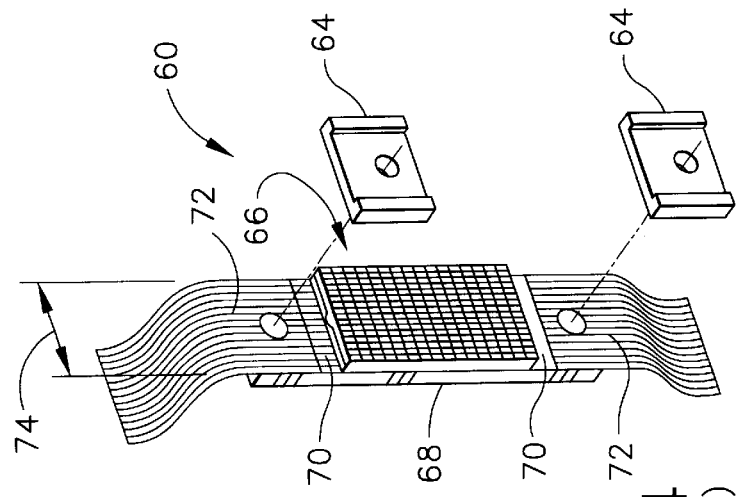
FIG. 4 is a perspective view of a single prior art module.

FIG. 3 is a perspective view of a prior art detector array 58 that includes a plurality of prior art modules 60. FIG. 4 is a perspective view of a single prior art module 60. Each module 60 includes a plurality of detector cells. Each detector module 60 is secured to a detector housing 62 by plates 64. Each module 60 includes a multidimensional scintillator array 66 and a high density semiconductor array (not visible). Scintillator array 66 includes a plurality of scintillation elements arranged in an array, and the semiconductor array includes a plurality of photodiodes arranged in an identical array. The photodiodes are deposited, or bonded on a substrate 68, and scintillator array 66 is positioned over and secured to substrate 68.

A switch and decoder apparatus 70 is coupled to the photodiode array. The photodiodes are optically coupled to scintillator array 66 and have electrical output lines for transmitting signals representative of the light output by scintillator array 66. Particularly, each photodiode produces a separate low level analog output signal that is a measurement of the beam attenuation for a specific scintillator of scintillator array 66.

Switch and decoder apparatus 70 is a multidimensional semiconductor switch array of similar width as the photodiode array, and switch and decoder apparatus 70 is coupled in electric circuit between the semiconductor array and a DAS. Switch and decoder apparatus 70 includes a plurality of field effect transistors (FETs) arranged as a multidimensional array. Each FET includes an input line electrically connected to one of the respective photodiode output lines, an output line, and a control line (not shown). FET output and control lines are electrically connected to the DAS via a flexible electrical cable 72. Particularly, about one-half of photodiode output lines are electrically connected to each FET input line on one side of the array with the other one-half of photodiode output lines electrically connected to the FET input lines on the other side of the array. Scintillator array 66, switch and decoder apparatus 70, and flexible cable 72 all have an approximate equal width 74.

Switch and decoder apparatus 70 controls the operation of the FETs to enable, disable, or combine photodiode outputs in accordance with a desired number of slices and slice resolutions for each slice. Switch and decoder apparatus 70, in one embodiment, is a decoder chip or a FET controller as known in the art, and switch and decoder apparatus 70 includes a plurality of output and control lines coupled to the FETs and the DAS. Particularly, the decoder outputs are electrically connected to the switch apparatus control lines to enable the FETs to transmit the proper data. The decoder control lines are electrically connected to the FET control lines and determine which of the outputs will be enabled. Utilizing switch and decoder apparatus 70, specific FETs are enabled, disabled, or have their outputs combined such that specific photodiode outputs are electrically connected to the DAS.

Figure 5:
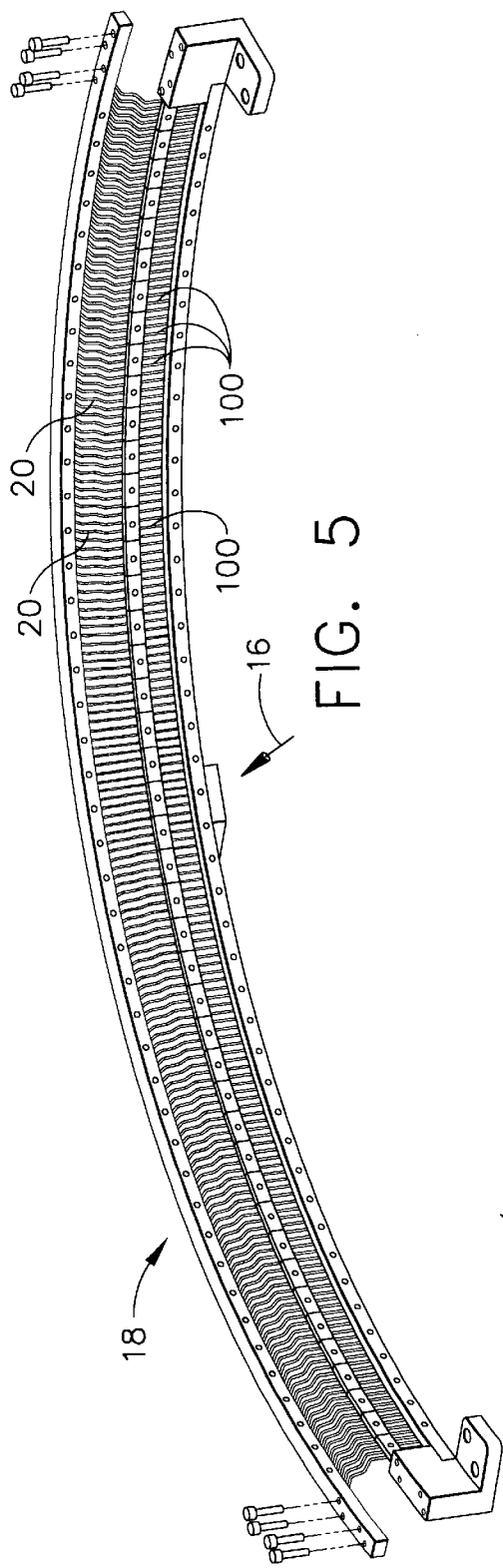
FIG. 5 is a perspective view of the detector array shown in FIG. 1.
Figure 6:
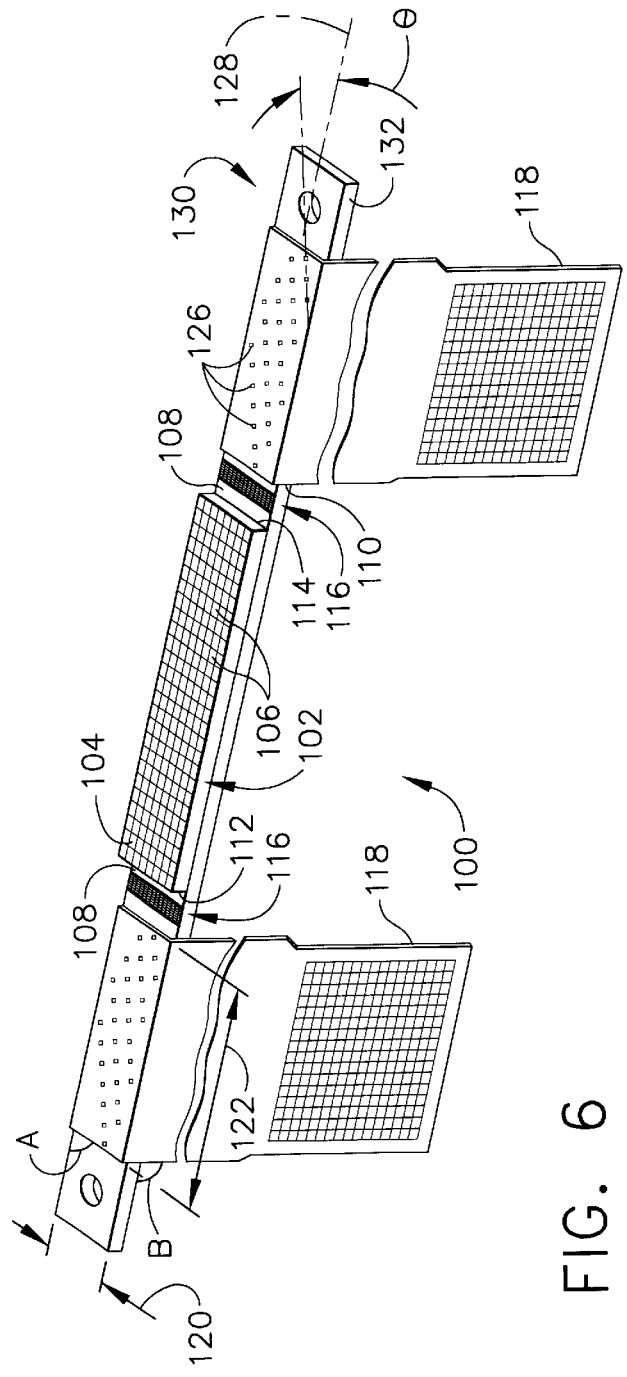
FIG. 6 is a perspective view of a single detector module shown in FIG. 5 having a high density flex interconnect.

FIG. 5 is a perspective view of detector array 18 (shown in FIG. 1). Detector array 18 includes a plurality of detector module assemblies 100 (also referred to as detector modules), each module including an array of detector elements 20. FIG. 6 is a perspective view of a single detector module 100 including a high-density photosensor array 102 and a multidimensional scintillator array 104 positioned above and adjacent to photosensory array 102. Particularly, scintillator array 104 includes a plurality of scintillator elements (not shown), while photosensor array 102 includes a plurality of photodiodes 106, and a switch and decoder apparatus 108. In one embodiment, photodiodes 106 are individual photodiodes. In another embodiment, photodiodes 106 are deposited or bonded on a substrate 110. Scintillator array 104 is positioned over or adjacent photodiodes 106, and photodiodes 106 are optically coupled to scintillator array 104 and have electrical output lines for transmitting signals representative of the light output by scintillator array 104. Each photodiode 106 produces a separate low level analog output signal that is a measurement of beam attenuation as measured by a specific scintillator of the scintillator array. Photodiode output lines (not shown) may, for example, be physically located on one side of module 100 or on a plurality of sides of module 100. In another embodiment, the photodiode outputs are located at opposing sides of photodiode array 102.

In one embodiment, as shown in FIG. 5, detector array 18 includes fifty-seven detector modules 100. Each detector module 100 includes a photosensor array 102 and scintillator array 104, each having a detector element 20 array size of 16×16. As a result, array 18 is segmented into 16 rows and 912 columns (16×57 modules) allowing up to N=16 simultaneous slices of data to be collected along a z-axis with each rotation of gantry 12, where the z-axis is an axis of rotation of the gantry.

Switch and decoder apparatus 108 is a multidimensional semiconductor switch array. Switch and decoder apparatus 108 is coupled between photosensor array 102 and DAS 32. Switch and decoder apparatus 108, in one embodiment, includes two semiconductor switch arrays 112 and 114. Switch arrays 112 and 114 each include a plurality of field effect transistors (FETS) 116 arranged as a multidimensional array. Each FET 116 includes an input electrically connected to one of the respective photodiode output lines, an output, and a control (not shown) arranged as a multidimensional array.

FET outputs and controls are connected to lines that are electrically connected to DAS 32 via a flexible electrical cable 118. Photosensor array 102, scintillator array 104, and switch and decoder apparatus 108 all have an approximate equal width 120. Flexible cable 118 has a width 122 different from width 120. In an exemplary embodiment, width 122 is greater than width 120. In one embodiment, width 122 is at least 125% width 120. Alternatively, width 122 is at least 150% width 120. In other embodiments, width 122 is at least twice width 120.

Additionally, flexible cable 118 receives data from a plurality of lower density area of contacts 126 arranged in rows and columns extending parallel to or at an oblique angle (θ) to a longitudinal axis 128 of module 100. In one embodiment θ is 0, and in another embodiment θ is at least 10°. Alternatively, θ is at least 20°. Contacts 126 form a flex circuit 130 which is mounted on a ceramic base 132 and which is rotated 90 degrees to the prior art design. This rotation allows the use of wider flexes thereby reducing the flex run pitch densities. In one embodiment, flex circuit 130 is thin to allow flex circuit 130 to be sandwiched between adjacent detector modules 100. In an alternative embodiment, ceramic base 132 has a step in the area of flex circuit 130 to eliminate the need for a thinned flex. In an exemplary embodiment, ceramic base 132 has radial edges to reduce a flex bend radius. The flex and associated interconnects are affixed to the ceramic base is by one of a solder reflux, an anisotropic conductive film (ACF) or an elastomeric connector with a clamp. In an alternative embodiment, a bumps and dimples contact is used.

A diode is extended under the flex and contains a two dimensional (2D) array of interconnects. In an exemplary embodiment, FET array 116 is a chip on the diode. Alternatively FET array 116 is mounted to flexible cable 118. In another embodiment, FET array 116 is included in DAS 32. Additionally, one embodiment uses a single DAS channel per detector cell. The diode can be wire bonded to a FET chip and then the FET chip is extended under flexible cable 118 and incorporate a 2D array of interconnects. Also, the diode can be wire bonded to a separate silicon chip that extends under the flex circuit accomplishing the same effect. A ceramic with a step can be utilized in both of the latter approaches. The connection from this 2D set of interconnects to the flexible circuit can be accomplished in a number of ways. These include a ball grid array with a solder reflow process, a set of pads below the flex, a two dimensional fine pitch elastomer interposer or thermal bonding with an ACF film or other means.

In an exemplary embodiment, about one-half of the photodiode output lines are electrically connected to each FET input line of switch 110 with the other one-half of photodiode output lines electrically connected to DAS 32 via flexible electrical cable 118. Particularly about one-half of the photodiode output lines are electrically connected to each FET input line of switch 110 with the other one-half of photodiode output lines electrically connected to FET input lines of switch 110. Flexible electrical cable 118 is thus electrically coupled to photosensor array 102 and is attached, for example, by wire bonding.

Figure 7:
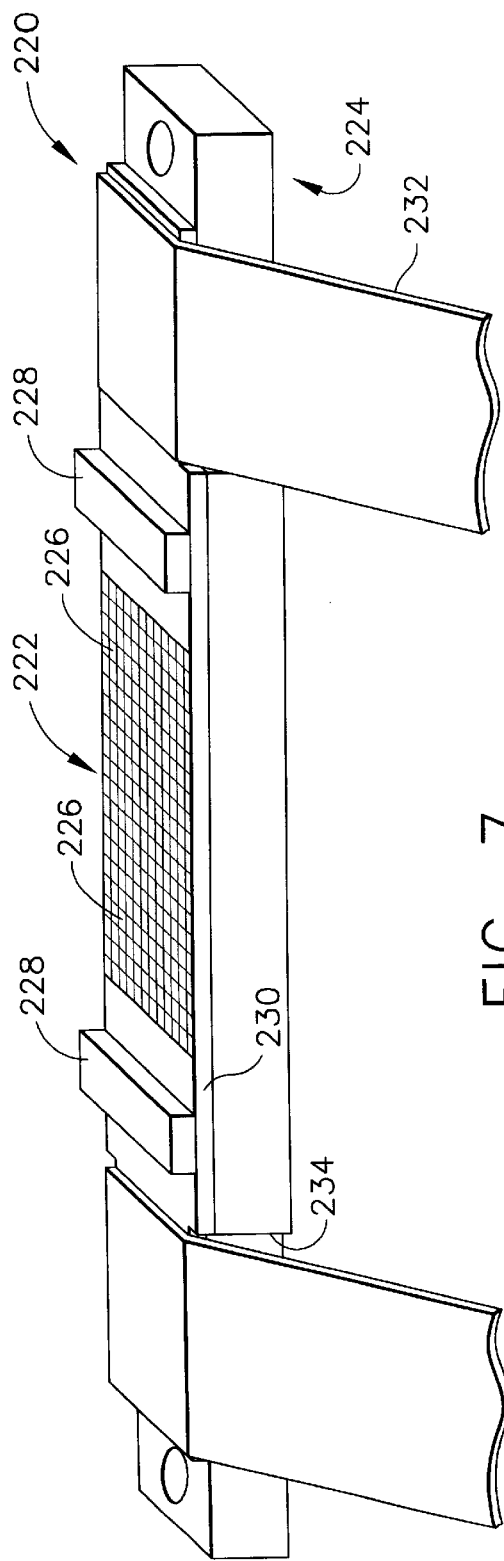
FIG. 7 is a perspective view of a module similar to the module depicted in FIG. 6.

FIG. 7 depicts a CT module having a high density flex interconnect 220, where the module has a photodiode chip 222 mounted on a substrate 224 with a diode array 226 cut in half to illustrate the use of 6 inch wafer chips which are readily available. Alternatively, diode array 226 is not cut in half. Two FET chips 228 are mounted directly on the diode silicon chip 226 ("flip chip design") one at each end of the module. The diode silicon chip extends under the flex atop the ceramic base 224. The flex circuit 232 bends 90 degrees off of each side. The two dimensional array interconnect 220 is located on the underside of the flex and on the top of the silicon. This connection uses solder reflow, or an anisotropic conductive film (ACF) or an elastomer connection with clamps or a bumps and dimples connection. In one embodiment, a cutout 234 is made on the sides of the module for facilitating the connection.

Figure 8:
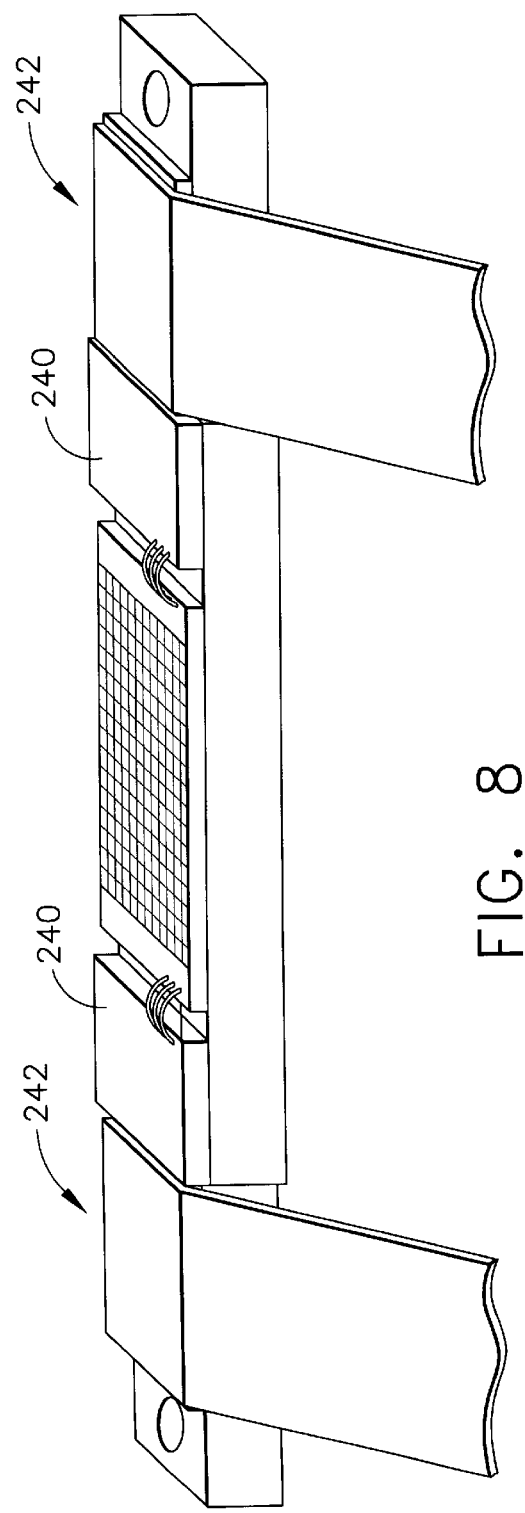
FIG. 8 is a perspective view of a module similar to the module depicted in FIG. 6.
Figure 11:
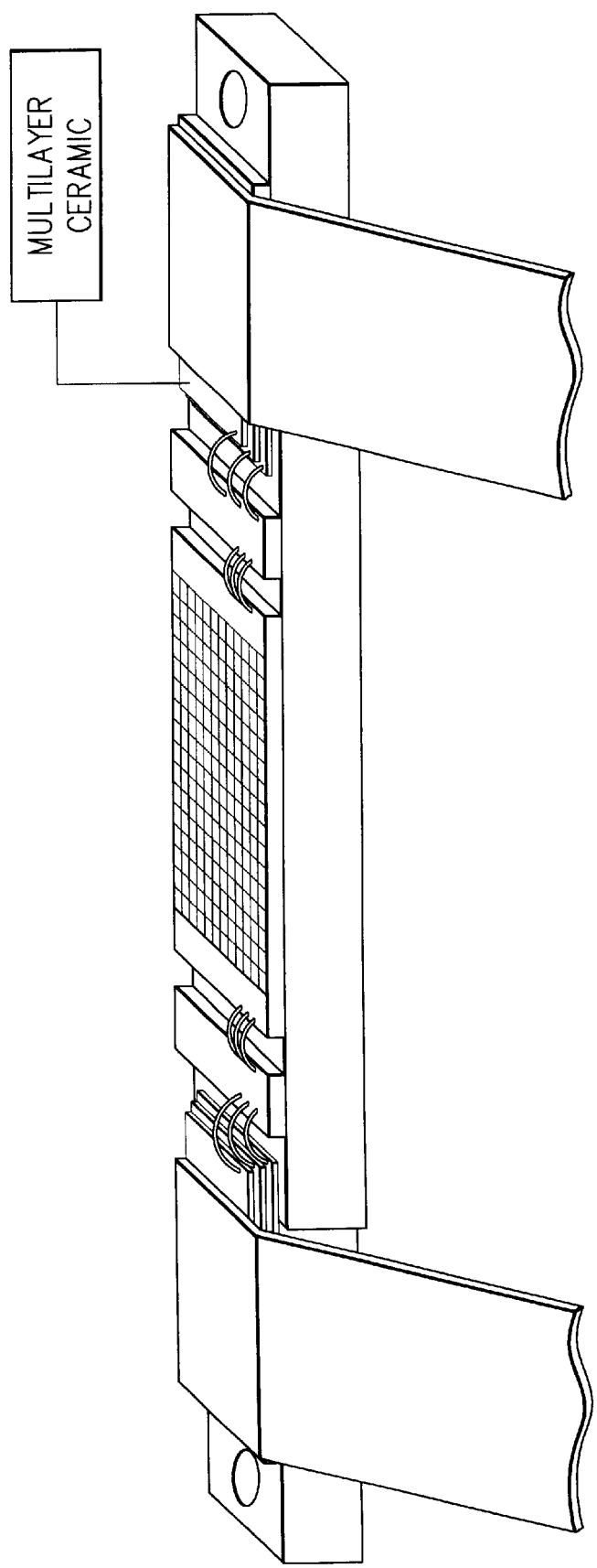
FIG. 11 is a perspective view of a module similar to the module depicted in FIG. 6.

FIG. 8 illustrates a module similar to that depicted in FIGS. 6 and 7 with the diode chip being shorter in FIG. 8 than in FIG. 7. Also, in FIG. 8 a FET chip 240 extends under a flex 242, and FET chip 240 is used as a signal run extender and for 90 degree run bends. FIG. 9 depicts a module similar to that depicted in FIG. 6 however, this embodiment illustrates a FET chip 250 being built as part of a diode chip 252. A separate silicon connector chip 254 with no active circuitry extends under the high density interconnect. A printed wiring board (PWB, not shown) may be employed as an alternative to a silicon chip. The silicon chip or PWB is used as a signal run extender and for 90 degree run bends. FIG. 10 depicts a module similar to that depicted in FIG. 6 but a plurality of separate FET switches 260 are provided. In one embodiment, FET switches 260 are glued onto the flex itself using a known adhesive. FIG. 11 depicts a module similar to that depicted in FIGS. 6 and 10 wherein the ceramic layer is a multilayer ceramic.

The modules illustrated in FIGS. 6–11 are connected to the detector array 18 of FIGS. 1 and 5 by mechanically affixing the module to the array. Holes are provided on the substrate of the module. The flex high density interconnect is electrically connected to the DAS by attaching the flex to the DAS system whereby electrical signals from the detector module are transmitted to the DAS system.

Accordingly, an improved interconnect/flex design is described which eliminate the density limits currently existing in known detector modules. This allows for CT detectors with larger coverage, more slices, and smaller cells in two dimensions. In making the above embodiments, bonding of the diodes, FET chips, and high density flex interconnect to a silicon chip and/or ceramic base is carried out by methods known to those of skill in the art.

While the invention has been described in terms of various specific embodiments, those skilled in the art will recognize that the invention can be practiced with modification within the spirit and scope of the claims.

What is claimed is:

1. A detector module comprising:
   a photosensor array having a first width; and
   a flexible cable operationally coupled to said photosensor array, said cable having a width greater then said first width.

2. A module in accordance with claim 1 wherein said cable having a width greater then said first width by at least 25%.

3. A module in accordance with claim 1 wherein said cable having a width greater then said first width by at least 50%.

4. A module in accordance with claim 1 wherein said cable having a width greater then said first width by at least 100%.

5. A module in accordance with claim 1 further comprising a plurality of contacts forming a two dimensional array extending under said flexible cable.

6. A module in accordance with claim 5 wherein said contacts extend at an angle of at least 10° from a longitudinal axis of a ceramic base supporting said photosensor array.

7. A module in accordance with claim 5 wherein said contacts extend at an angle of at least 20° from a longitudinal axis of a ceramic base supporting said photosensor array.

8. A photosensor module configured for use in a computed tomography system having a DAS system for receiving data, said module comprising:
   a substrate having a photodiode array thereon optically coupled to a scintillator array;
   a FET chip electrically connected to said photodiode array and mounted on said substrate; and
   a high density interconnect, and a flex circuit connected to said DAS system, said flex interconnect is mounted on said substrate wherein the longitudinal axis of the flex circuit is perpendicular to the horizontal axis of said substrate and diode.

9. A photosensor module in accordance with claim 8 wherein the longitudinal axis of the flex circuit is bent 90 degrees to the horizontal axis of said substrate.

10. A photosensor module in accordance with claim 8 wherein said flex interconnect extends at least one of parallel to the horizontal axis of said substrate and obliquely to the horizontal axis of said substrate.

11. A photosensor module in accordance with claim 8 wherein said flex interconnect extends obliquely to the horizontal axis of said substrate at an angle of at least approximately 10°.

12. A photosensor module in accordance with claim 8 wherein said flex interconnect extends obliquely to the horizontal axis of said substrate at an angle of at least approximately 20°.

13. A photosensor module in accordance with claim 8 wherein said substrate comprises a ceramic material.

14. A Computed Tomographic (CT) system comprising:
   a radiation source; and
   a detector array positioned to receive radiation from said source, said detector array comprising a plurality of detector modules each comprising:
   a photosensor array having a first width; and
   a flexible cable operationally coupled to said photosensor array, said cable having a width greater then said first width.

15. A CT system in accordance with claim 14 wherein said cable having a width greater then said first width by at least 50%.

16. A CT system in accordance with claim 14 wherein said cable having a width greater then said first width by at least 100%.

17. A CT system in accordance with claim 14 wherein each said module further comprises a plurality of contacts extending under said flexible cable at least one of parallel to a longitudinal axis of a ceramic base supporting said photosensor array and obliquely to the longitudinal axis of the ceramic base supporting said photosensor array.

18. A CT system in accordance with claim 17 wherein said contacts extend at an angle of at least 10° from said longitudinal axis.

19. A CT system in accordance with claim 18 wherein said contacts extend at an angle of at least 20° from said longitudinal axis.

20. A CT system in accordance with claim 14 wherein each said flexible cable extends perpendicularly a longitudinal axis of a ceramic base supporting said photosensor array.

* * * * *

UNITED STATES PATENT AND TRADEMARK OFFICE
CERTIFICATE OF CORRECTION

PATENT NO. : 6,522,715 B2
DATED : February 18, 2003
INVENTOR(S) : Hoffman et al.

It is certified that error appears in the above-identified patent and that said Letters Patent is hereby corrected as shown below:

Title page,
Item [57], ABSTRACT,
Line 3, delete "then" and insert therefor -- than --.

Column 1,
Lines 35 and 53, delete "then" and insert therefor -- than --.

Column 5,
Lines 62 and 66, delete "110" and insert therefor -- 108 --.

Column 6,
Line 45, delete "eliminate" and insert therefor -- eliminates --.
Lines 60, 63 and 66, delete "then" and insert therefor -- than --.

Column 7,
Line 2, delete "then" and insert therefor -- than --.

Column 8,
Lines 13, 16 and 19, delete "then" and insert therefor -- than --.

Signed and Sealed this

Twelfth Day of August, 2003

JAMES E. ROGAN
*Director of the United States Patent and Trademark Office*